United States Patent [19]
Chin

[11] Patent Number: 5,924,982
[45] Date of Patent: Jul. 20, 1999

[54] OXIMETER SENSOR WITH USER-MODIFIABLE COLOR SURFACE

[75] Inventor: Rodney P. Chin, Oakland, Calif.

[73] Assignee: Nellcor Puritan Bennett Incorporated, Pleasanton, Calif.

[21] Appl. No.: 08/903,500

[22] Filed: Jul. 30, 1997

[51] Int. Cl.⁶ ...................................................... A61B 5/00
[52] U.S. Cl. ........................ 600/310; 600/322; 600/323
[58] Field of Search ................................. 600/310, 322, 600/323, 326, 331, 340, 344, 372, 382, 384, 392, 473, 476, 479, 480, 485, 500

[56] References Cited

U.S. PATENT DOCUMENTS

| | | | |
|---|---|---|---|
| 4,830,014 | 5/1989 | Goodman et al. | 600/310 |
| 5,217,012 | 6/1993 | Young et al. | 600/310 |
| 5,402,777 | 4/1995 | Warring et al. | 600/334 |
| 5,619,992 | 4/1997 | Guthrie et al. | 600/323 |
| 5,673,693 | 10/1997 | Solenberger | 600/323 |

*Primary Examiner*—Lee Cohen
*Assistant Examiner*—Bryan K. Yarnell
*Attorney, Agent, or Firm*—Townsend and Townsend and Crew LLP

[57] ABSTRACT

An oximeter sensor with an emitter and a detector, and a sensor body surface having a first color proximate to at least one of the emitter or detector. The color can be modified by a user to adapt the sensor to be optimized for maximal signal strength or insensitivity to skin pigmentation variability or accuracy. In a preferred embodiment, a pulse oximeter sensor with an outer layer which is colored gray or black in the region of the emitters and detector and in between can be peeled-away to reveal a substantially white layer. Alternately, a white colored layer could peeled-away to reveal a gray or black layer. Alternately, more than one peeled-away layer could be used to provide a range of colors.

10 Claims, 2 Drawing Sheets

OXIMETER SENSOR WITH USER-MODIFIABLE COLOR SURFACE

BACKGROUND OF THE INVENTION

The present invention relates to oximeter sensors, in particular to pulse oximeter sensors with a colored contact surface.

In a conventional oximetry sensor, light is typically emitted by red and infrared emitters and detected by a photodetector. The light scatters through the tissue between the emitters and the detector. There are two types of paths that the photons can generally take. One type of photon path resides mostly inside the blood-perfused tissue without seeing the effects of the skin. The other type of photon path experiences a significant effect of the skin surface which contains skin pigment (melanin). It has been shown that melanin absorbs red light to a greater degree than near infrared light. Accordingly, a pulse oximeter sensor calibrated for its red and infrared emitters for a particular amount of skin pigmentation will produce an erroneous result when the sensor is applied to a patient having a different amount of skin pigmentation. The skin pigmentation will absorb more red light than infrared light, causing a greater variance in the calibration from the correct one.

For example, a pulse oximeter sensor may be calibrated for light pigmentation skin, with a sensor body surface that is white. Such a sensor will lose accuracy when it is applied to a patient having a darker skin pigmentation. One approach to addressing this problem is to use a sensor body having a dark (gray or black) colored surface. This reduces the amount of secondary scattered contribution associated with the skin pigmentation making the calibration more consistent and less dependent on the degree of skin pigmentation. However, this also reduces the strength of the pulsatile (AC) component of the signal. Accordingly, a compromise must be made between accuracy and pulsatile signal strength. The latter is desired in the case of a low-perfusion application.

SUMMARY OF THE INVENTION

The present invention provides an oximeter sensor with an emitter and a detector, and a sensor body surface having a first color proximate to at least one of the emitters or detector. The present invention provides that the color can be modified by a user to adapt the sensor to a different optimization or compensate for skin pigmentation.

In a preferred embodiment, a pulse oximeter sensor with an outer layer which is colored gray or black in the region of the emitters and detector and in between can be peeled-away to reveal a substantially white layer. Alternately, a white colored layer could peeled-away to reveal a gray or black layer. Alternately, more than one peeled-away layer could be used to provide a range of colors.

In one embodiment, peeling away a layer could break a built in "fuse", which could alter the value of a calibration resistor. The altered calibration resistor would provide an appropriate value to select coefficients in a oximeter corresponding to the expected secondary scattering effect for the particular color exposed.

For a fuller understanding of the nature and advantages of the invention, reference should be made to the following description taken in conjunction with the accompanying drawings.

DESCRIPTION OF THE PREFERRED EMBODIMENT

Figure 1:
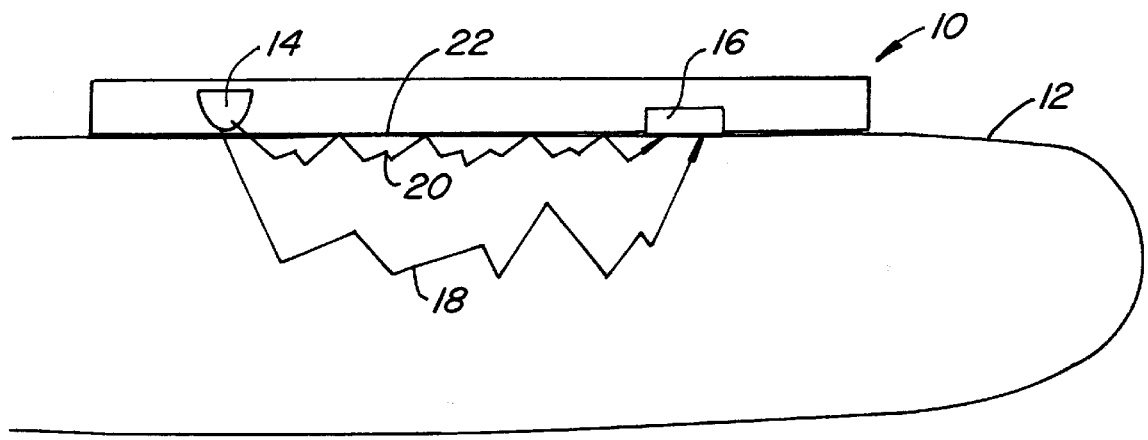
FIGS. 1A and 1B are cross sectional views of a sensor applied to a patient's finger illustrating primary and secondary scattering.
Figure 1A:
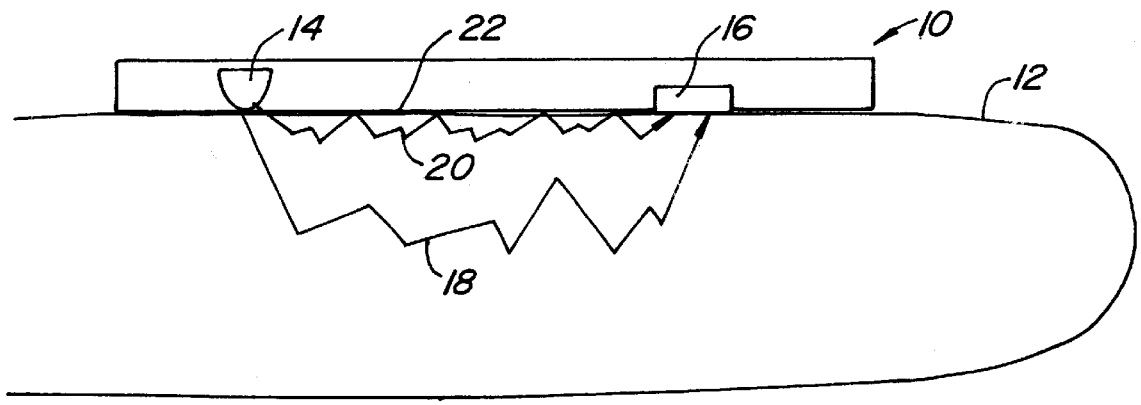
Figure 1B:
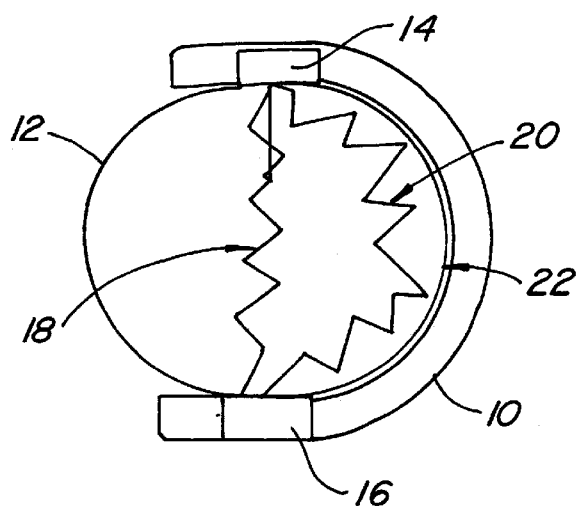

FIGS. 1A and 1B illustrate a sensor 10 applied to a patient finger 12. Sensor 10 includes an emitter 14 and a photodetector 16. As illustrated, photons from the emitter 14 can take various paths through finger 12. A particular path 18 is shown which travels deep through the body of the tissue before reaching detector 16. This is an illustration of primary scattering. An alternate path 20 travels along the surface of the finger, reflecting off of a contact surface 22 of sensor 10. This path is an example of secondary scattering. If the surface 22 of sensor 10 is black, for instance, it will absorb both red light and infrared. Accordingly, the amount of secondary scattering will be reduced, since more of photons taking paths similar to 20 will be absorbed, rather than reaching photodetector 16. The signal would be dominated by photons taking path 18.

Figure 2A:
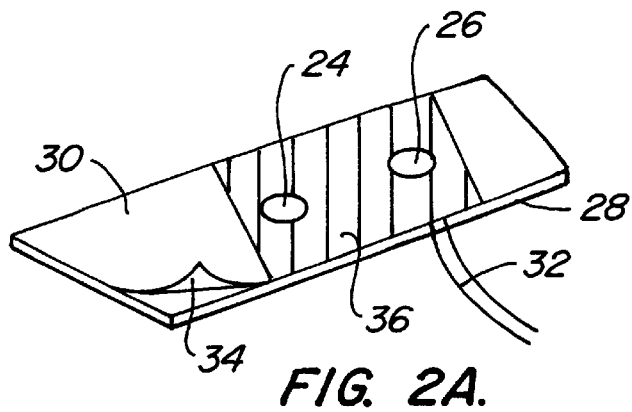
FIGS. 2A and 2B illustrate one embodiment of the invention showing a peel-away layer.

FIG. 2A illustrates one embodiment of a sensor according to the present invention. The sensor includes an emitter 24 and detector 26 mounted on a sensor body having a first layer 28 and a second, peelable layer 30. Cable 32 connects to the electronic components on the sensor, such as the emitter and detector. As can be seen at a corner 34, layer 30 can be peeled away, as illustrated. A center portion 36 of layer 30 is shown with a different coloring than the end portions. Alternately, the entire layer could be a particular color.

Figure 2B:
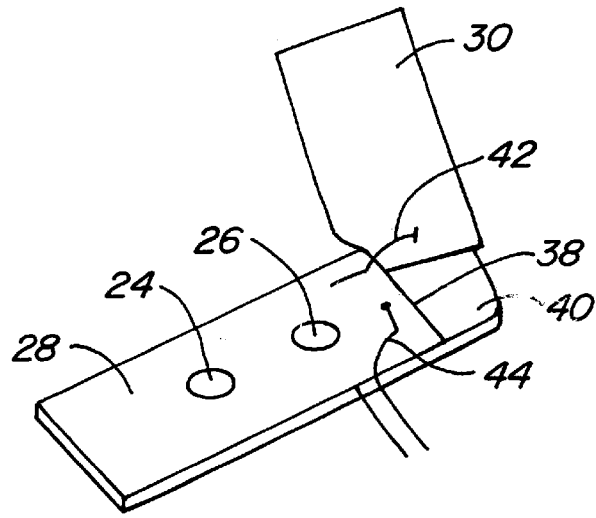

As shown in FIG. 2B, layer 30 is almost entirely peeled away, revealing a top surface of layer 28 which is a different color than the color of area 36 of 30.

In the embodiment shown, both layers 30 and 28 have an adhesive for attaching to the patient of a skin. In the embodiment shown, layer 30 tears along a line 38, with a portion 40 permanently bonded to underlying layer 28. This embodiment makes it more difficult for the layers to become inadvertently separated, since a portion of layer 30 will always be permanently bonded. Alternately, the entire layer 30 could be peeled off.

Also shown in FIG. 2B is a "fuse" consisting of a wire trace having an end 42 which has broken away from portion 44 to which was previously connected. Such a break can be used to convey a simple digital signal to an oximeter monitor indicating that the layer has been peeled away. Alternately, the fuse can be broken to change the value of a calibration resistor incorporated in the sensor.

Figure 3A:
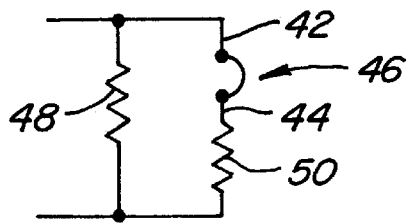
FIGS. 3A and 3B illustrate different calibration resistor configurations with a fuse which can be broken with a peel-away layer.
Figure 3B:
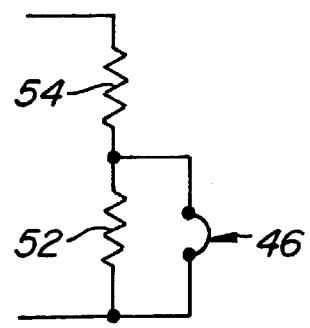

FIGS. 3A and 3B illustrate different circuit configurations for fuse 46 and its connecting wires 42 and 44. In the first embodiment of FIG. 3A, a first calibration resistor 48 is normally connected in parallel with a second calibration resistor 50. The parallel combination provides an appropriate calibration indication to an oximeter monitor when layer 30 is attached. When layer 30 is removed, fuse 46 is broken, effectively taking resistor 50 out of in parallel with resistor 48. Thus, the value of the calibration resistor is changed to that of resistor 48 alone, giving a higher resistor value which can select appropriate coefficients for the color of layer 28.

FIG. 3B shows an alternate embodiment in which fuse 46 normally short circuits a second resistor 52 connected in series with the first resistor 54. Thus, the resistance would be normally that of resistor 54, and when the layer is peeled away, the resistor becomes the combined value of resistors 54 and 52. This also gives a greater resistor value when the layer is peeled away. Alternately, an arrangement which gives a lower resistance when the fuse is broken could be used.

In one embodiment, layer 30 is laminated to layer 28 with an adhesive which allows user separation, and also will provide an appropriate adhesive contact to a patient's skin. In an alternate embodiment, multiple laminate layers could be employed, each having its own built in fuse, which could connect or disconnect multiple resistors in series, in parallel, or in any combination thereof.

In one embodiment the coloring is provided by a printing process in which black pixels are printed on layer 30. The density of the black pixels can be chosen to provide the level of gray that is desired.

As will be understood by those of skill in the art, the present invention may be embodied in other specific forms without departing from the spirit or essential characteristics thereof. For example, the means for altering color could be an electro-optical device which changes color using an electrical signal. Accordingly, the foregoing description is meant to be illustrative, but not limiting, of the scope of the invention which is set forth in the following claims.

What is claimed is:

1. An oximeter sensor comprising:
   a sensor body having a patient contact surface for contacting a patient when the sensor is in use;
   at least one emitter mounted in said sensor body;
   at least one detector mounted in said sensor body; and
   means for altering a color of at least a portion of said patient contact surface such that said sensor is usable with different colors for different patients.

2. The oximeter sensor of claim 1 wherein said portion of said patient contact surface is proximate to said emitter or said detector.

3. The oximeter sensor of claim 1 wherein said means for altering comprises a peel-away first layer having a first color in said portion different from a second color of a second, underlying layer in said portion.

4. The oximeter sensor of claim 3 wherein said first color is gray or black, and said second color is substantially white.

5. An oximeter sensor comprising:
   a sensor body having a patient contact surface;
   at least one emitter mounted in said sensor body;
   at least one detector mounted in said sensor body;
   means for altering a color of at least a portion of said patient contact surface; and
   means for generating a calibration indicator upon said altering of a color.

6. An oximeter sensor comprising:
   a sensor body having a patient contact surface;
   at least one emitter mounted in said sensor body;
   at least one detector mounted in said sensor body; and
   means for altering a color of at least a portion of said patient contact surface;
   wherein said means for altering comprises an electro-optical device which changes color using an electrical signal.

7. An oximeter sensor comprising:
   a sensor body having a patient contact surface for contacting a patient when the sensor is in use;
   at least one emitter mounted in said sensor body;
   at least one detector mounted in said sensor body; and
   a peel-away first layer on said patient contact surface having a first color in at least a portion of said patient contact surface proximate to said emitter or said detector, said first color being different from a second color of a second, underlying layer in said portion, said sensor being usable with either said first layer or said second layer, such that said sensor is usable with different colors for different patients.

8. An oximeter sensor comprising:
   a sensor body having a patient contact surface;
   at least one emitter mounted in said sensor body;
   at least one detector mounted in said sensor body; and
   a peel-away first layer having a first color in at least a portion of said patient contact surface proximate to said emitter or said detector, said first color being different from a second color of a second, underlying layer in said portion;
   wherein said first color is gray or black, and said second color is substantially white.

9. The oximeter sensor of claim 8 wherein the gray color is produced by white and black pixels with the density of black pixels determining the level of gray.

10. An oximeter sensor comprising:
    a sensor body having a patient contact surface;
    at least one emitter mounted in said sensor body;
    at least one detector mounted in said sensor body;
    a peel-away first layer having a first color in at least a portion of said patient contact surface proximate to said emitter or said detector, said first color being different from a second color of a second, underlying layer in said portion;
    a calibration indicator mounted in said sensor body; and
    means for modifying said calibration indicator upon a peeling away of said first layer.

\* \* \* \* \*